United States Patent
Tominaga et al.

(10) Patent No.: US 9,709,488 B2
(45) Date of Patent: Jul. 18, 2017

(54) SENSOR UNIT

(71) Applicant: NEC Corporation, Tokyo (JP)

(72) Inventors: Shin Tominaga, Tokyo (JP); Yasuhiro Sasaki, Tokyo (JP); Masatake Takahashi, Tokyo (JP); Junichiro Mataga, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 14/917,725

(22) PCT Filed: Jun. 26, 2014

(86) PCT No.: PCT/JP2014/066946
§ 371 (c)(1),
(2) Date: Mar. 9, 2016

(87) PCT Pub. No.: WO2015/037306
PCT Pub. Date: Mar. 19, 2015

(65) Prior Publication Data
US 2016/0216203 A1   Jul. 28, 2016

(30) Foreign Application Priority Data
Sep. 12, 2013 (JP) .................. 2013-189462

(51) Int. Cl.
*G01J 3/40* (2006.01)
*G01N 21/41* (2006.01)
(Continued)

(52) U.S. Cl.
CPC ............ *G01N 21/41* (2013.01); *G01J 3/1838* (2013.01); *G01J 3/36* (2013.01); *G01J 5/02* (2013.01);
(Continued)

(58) Field of Classification Search
CPC .... G01N 21/41; G01J 5/02; G01J 3/02; G01J 3/28; G01J 3/18
See application file for complete search history.

(56) References Cited

U.S. PATENT DOCUMENTS 7,307,788 B2   12/2007   Boettiger et al.
8,525,199 B2    9/2013   Konishi
(Continued)

FOREIGN PATENT DOCUMENTS

JP   06-313857   11/1994
JP   11-281811   10/1999
(Continued)

OTHER PUBLICATIONS

International Search Report, PCT/JP2014/066946, Oct. 7, 2014.

*Primary Examiner* — Abdullahi Nur
(74) *Attorney, Agent, or Firm* — Young & Thompson

(57) ABSTRACT

A sensor unit (100) provided with a substrate (101), a plurality of light-receiving units (102) that are provided on the substrate (101) and detect light, and a diffraction grating layer (103) that is provided on the substrate (101) and the light-receiving units (102) and has at least two diffraction means for diffracting light of corresponding wavelengths and condensing the light onto the light-receiving units, wherein at least two of the diffraction means are composed from holograms formed on a first diffraction grating layer and at least a portion of the plurality of holograms formed on the first diffraction grating layer overlap at least partially with another adjacent hologram.

19 Claims, 14 Drawing Sheets

(51) Int. Cl.
  *G01J 3/36* (2006.01)
  *G02B 5/32* (2006.01)
  *H01L 31/0232* (2014.01)
  *H04N 9/04* (2006.01)
  *G01J 3/18* (2006.01)
  *G01J 5/02* (2006.01)
  *G02B 3/00* (2006.01)
  *G01J 3/28* (2006.01)

(52) U.S. Cl.
  CPC ............ *G02B 5/32* (2013.01); *H01L 31/0232* (2013.01); *H04N 9/045* (2013.01); *G01J 2003/2813* (2013.01); *G01N 2201/068* (2013.01); *G02B 3/0056* (2013.01); *G02B 3/0087* (2013.01); *H04N 2209/042* (2013.01)

(56) References Cited

U.S. PATENT DOCUMENTS

| | | | |
|---|---|---|---|
| 2002/0176037 A1* | 11/2002 | Li | G01J 3/14 349/95 |
| 2006/0091300 A1 | 5/2006 | Nishimura | |
| 2006/0119950 A1 | 6/2006 | Boettiger et al. | |
| 2008/0173793 A1 | 7/2008 | Mokhnatyuk | |
| 2009/0115011 A1 | 5/2009 | Ushiro et al. | |
| 2010/0025788 A1 | 2/2010 | Konishi | |

FOREIGN PATENT DOCUMENTS

| | | |
|---|---|---|
| JP | 2006-135320 | 5/2006 |
| JP | 2007-109801 | 4/2007 |
| JP | 2007-311413 | 11/2007 |
| JP | 2008-522245 | 6/2008 |
| WO | WO 2006/060298 | 6/2006 |
| WO | WO 2008/091534 | 7/2008 |

\* cited by examiner

SENSOR UNIT

TECHNICAL FIELD

The present invention relates to a sensor unit.

BACKGROUND ART

As a sensor for analyzing ingredients contained in a liquid or the like, a sensor for detecting light of a specific wavelength has already been used. The sensor irradiates a liquid under measurement with light emitted from a light source, such as an LED, and measures a transmitted, scattered or reflected amount in terms of each specific wavelength. Subsequently, the ingredients are identified by comparing the measurement result with intrinsic absorption and scattering characteristics of the targets of analysis as a function of wavelength.

On the other hand, as a result of the advance in information and telecommunication technology and the expansion of network infrastructure in recent years, there has been a new trend in sensor usage such as that for energy conservation in building air conditioning, for water quality management in waterworks and for grasping consumer behavior, where a sensor device with small size and high sensitivity is demanded, for the purpose of realizing a system which can make simultaneous use of a large number of sensors.

Related technologies are disclosed in Patent Literature 1 to Patent Literature 5.

An optical sensor described in Patent Literature 1 is composed of a microlens array, a color filter array and a sensor array. Light emitted from a light source is condensed by the microlens array, and accordingly becomes incident on the color filter array. Out of the light incident on the color filter array, only a specific wavelength component is transmitted by each filter of the color filter array, in accordance with the filter's transmission characteristics. Light transmitted by the color filter array becomes incident on the sensor array. From the sensor array, a voltage is outputted in accordance with the incident light amount.

Patent Literature 2 and Patent Literature 3 disclose a microlens array composed of a plurality of convex microlenses each arranged such that at least part of its periphery overlaps with neighboring microlenses.

Patent Literature 4 and Patent Literature 5 disclose a microlens array constructed by arranging a plurality of microlenses.

CITATION LIST

Patent Literature

[PTL 1] International Patent Publication Number WO/2006/060298
[PTL 2] Published Japanese translation of PCT application No. 2008-522245
[PTL 3] Japanese Patent Application Laid-Open No. 2007-311413
[PTL 4] Japanese Patent Application Laid-Open No. 2007-109801
[PTL 5] Japanese Patent Application Laid-Open No. 2006-135320

SUMMARY OF INVENTION

Technical Problem

The technologies described in Patent Literature 1, Patent Literature 4 and Patent Literature 5 have a problem of low light utilization efficiency. The reason is that, while the microlenses for taking in light are arranged in a manner to minimize the gaps between them in the lateral direction, it is impossible to make their stacking in the thickness direction of the optical sensor, that is, in the optical axis direction of incident light. It is not easy to fabricate a microlens array in which convex microlenses located in the same layer are stacked with each other, as in the technologies described in Patent Literature 2 and Patent Literature 3. The subject of the present invention is to provide a sensor unit which is excellent in light utilization efficiency.

Solution to Problem

According to the present invention, provided is a sensor unit comprising:
a substrate;
a plurality of light receiving parts arranged over the substrate and for detecting light; and
one or more diffraction grating layers arranged over the substrate and the light receiving parts, the diffraction grating layers having two or more diffraction means each for diffracting light of a corresponding wavelength and thereby condensing the light at a corresponding one of the light receiving parts, wherein:
at least two of the diffraction means are each constituted by a hologram formed in a first one of the diffraction grating layers; and
at least some of the plurality of holograms formed in the first diffraction grating layer each overlap at least partly with other ones of the plurality of holograms neighboring it.

Advantageous Effects of Invention

According to the present invention, a sensor unit having excellent light utilization efficiency is realized.

BRIEF DESCRIPTION OF DRAWINGS

The above-described and other objectives, features and advantages of the present invention will become further apparent from the following description of exemplary embodiments when taken with accompanying drawings.

DESCRIPTION OF EMBODIMENTS

Figure 1:
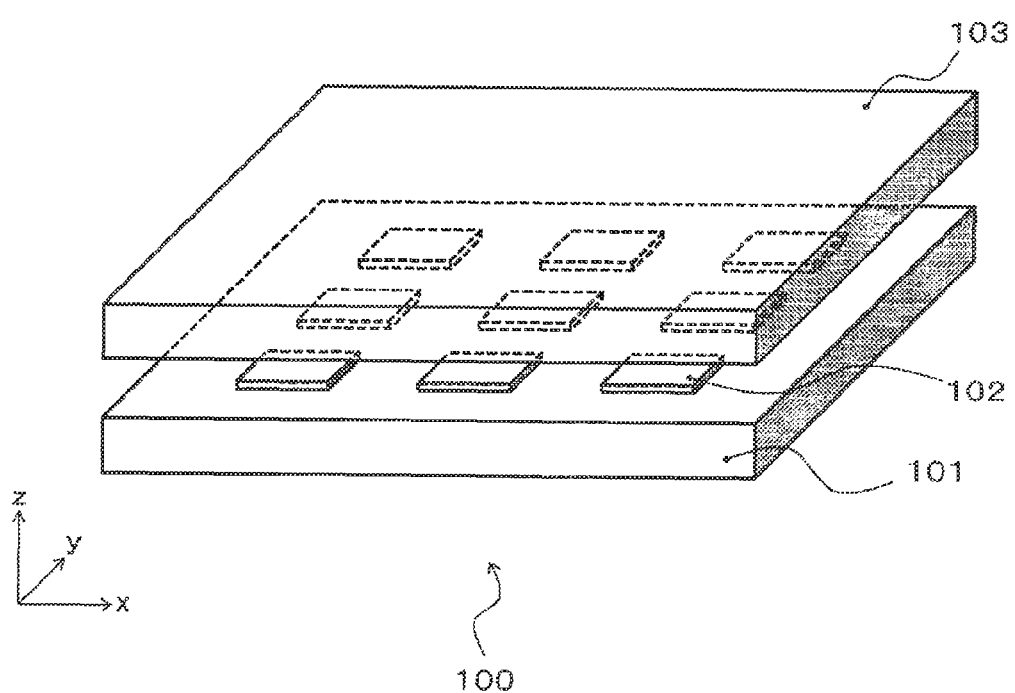
FIG. 1 a perspective view showing an optical sensor 100 of exemplary embodiments
FIG. 2 a cross-sectional view showing the optical sensor 100 of exemplary embodiments
FIG. 3 a plan view showing the optical sensor 100 of exemplary embodiments
FIG. 4 a cross-sectional view showing the optical sensor 100 of exemplary embodiments
FIG. 5 a cross-sectional view showing an optical sensor 100 of exemplary embodiments
FIG. 6 a cross-sectional view showing the optical sensor 100 of exemplary embodiments
FIG. 7 a cross-sectional view showing an optical sensor 100 of embodiments
FIG. 8 a cross-sectional view showing an optical sensor 100 of exemplary embodiments
FIG. 9 a cross-sectional view showing an optical sensor 100 of exemplary embodiments
FIG. 10 a cross-sectional view showing an optical sensor 100 of exemplary embodiments
FIG. 11 a plan view showing an optical sensor 100 of exemplary embodiments
FIG. 12 a plan view showing an optical sensor 100 of exemplary embodiments FIG. 13 a cross-sectional view showing an optical sensor 100 of exemplary embodiments FIG. 14 a cross-sectional view showing the optical sensor 100 of exemplary embodiments

Hereinafter, exemplary embodiments of the present invention will be described with reference to the drawings. In the following description, the same reference sign is assigned to constituent elements having the same function, and their descriptions may be omitted in some cases. In the drawings, it is difficult to illustrate layers included in an actual optical sensor in a precise scale or proportion. Therefore, the drawings showing optical sensors of the present invention are schematic ones, where sizes and thicknesses of the layers are not illustrated in the actual proportion. The x-, y- and z-directions are each common to all of the drawings.

In the following descriptions, when it is described that preferably the present invention satisfies a form or a condition, it is given just for describing a preferable form or condition, not being intended to exclude any other forms or conditions.

First Exemplary Embodiment

A sensor unit (optical sensor) of the present exemplary embodiment comprises a substrate, a plurality of light receiving parts and one or more diffraction grating layers. The light receiving parts are arranged on the substrate. The light receiving parts are configured in a manner to detect light. The diffraction grating layers are arranged over the substrate and the light receiving parts. The diffraction grating layers as a whole may be a single layer, or may be a layered structure composed of a plurality of layers stacked with each other. The diffraction grating layers have two or more diffraction means. The two or more diffraction means each diffract light of a corresponding wavelength, thereby condensing the light at a corresponding one of the light receiving parts. At least two of the diffraction means are each constituted by a hologram formed in a first one of the diffraction grating layers (a first diffraction grating layer). At least some of the diffraction means (holograms) formed in the first diffraction grating layer each overlap at least partly with other ones of the diffraction means (holograms) neighboring it. Here, "at least some of the diffraction means" means "at least a partial number of ones among the plurality of diffraction means". Also here, "overlap at least partly" means that "at least part of the diffraction means overlaps (with other diffraction means)". These assumptions are applied in all of the following descriptions.

At least one of the diffraction means may be formed in a second one of the diffraction grating layers, which is provided on the first diffraction grating layer. In that case, in the plan view, at least some of the diffraction means formed in the first diffraction grating layer each overlap at least partly with some of the diffraction means formed in the second diffraction grating layer. At least some of the diffraction means formed in the second diffraction grating layer may each be constituted by a hologram. Then, at least some of the plurality of diffraction means (holograms) formed in the second diffraction grating layer may each overlap at least partly with other ones of the plurality of diffraction means (holograms) neighboring it.

The sensor unit (light beam sensor) of the present exemplary embodiment may further comprise another diffraction grating layer on the second diffraction grating layer. In that case, in the plan view, at least some of the diffraction means formed in the another diffraction grating layer each overlap at least partly with some of the diffraction means formed in the first and/or second diffraction grating layers. At least some of the diffraction means formed in the another diffraction grating layer may each be constituted by a hologram. Then, at least some of the diffraction means (holograms) formed in the another diffraction grating layer may each overlap at least partly with other ones of the diffraction means (holograms) neighboring it.

At least one of the diffraction means formed in the diffraction grating layers may be constituted by a convex-concave part. That is, interference fringes may be generated by the convex-concave part. By changing the convex-concave pitch in accordance with a wavelength to diffract, a diffraction means for diffracting the desired wavelength can be realized. For example, a diffraction means constituted by a hologram and that by a microlens may coexist. When the diffraction grating layers as a whole are formed as a layered structure composed of a plurality of layers stacked with each other, in the plan view, a diffraction means constituted by a convex-concave part formed in one of the layers may overlap at least partly with diffraction means (convex-concave parts or holograms) formed in another one of the layers.

Hereinafter, a detail description will be given of the present exemplary embodiment, using drawings. FIG. 1 is a perspective view showing an optical sensor 100 according to the present exemplary embodiment. As shown in FIG. 1, the optical sensor 100 of the present exemplary embodiment comprises a substrate 101, a plurality of light receiving parts 102 and a diffraction grating layer structure 103.

The substrate 101 supports the light receiving parts 102. Each of the light receiving parts 102 shows a change in its physical property due to the energy of incident light, and accordingly outputs a voltage via an electrode and a wiring, which are not illustrated in the drawing. The diffraction grating layer structure 103 diffracts light incident from above in the drawing, thereby directing components of the light toward respective ones of the light receiving parts 102 located underneath.

Figure 2:
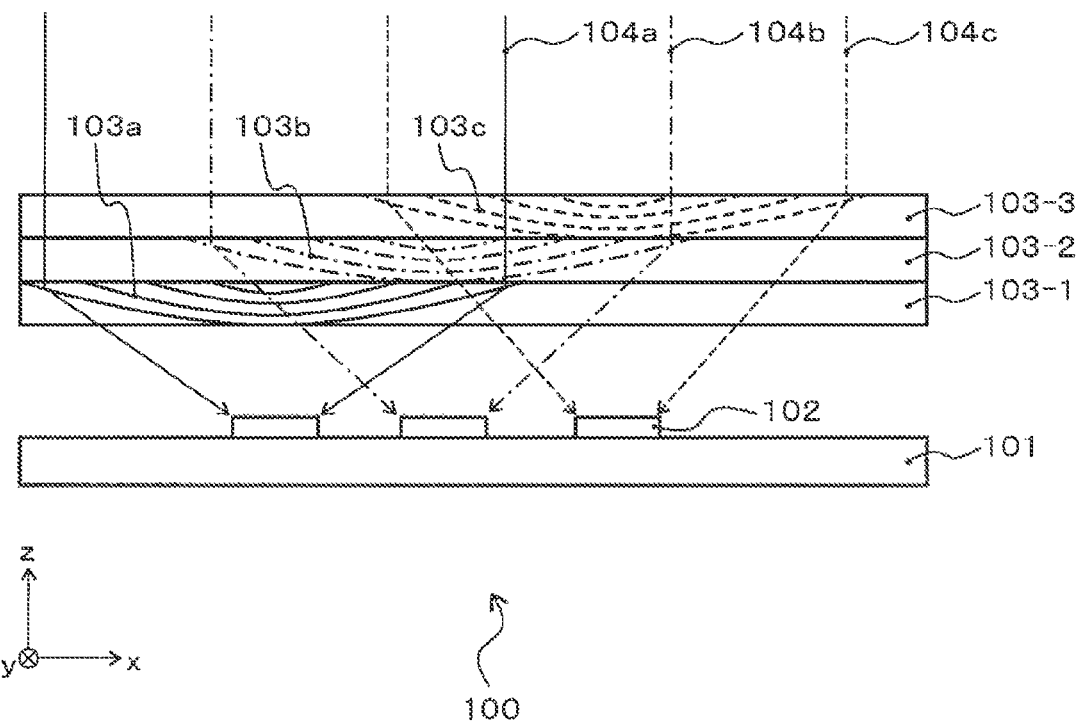
Figure 3:
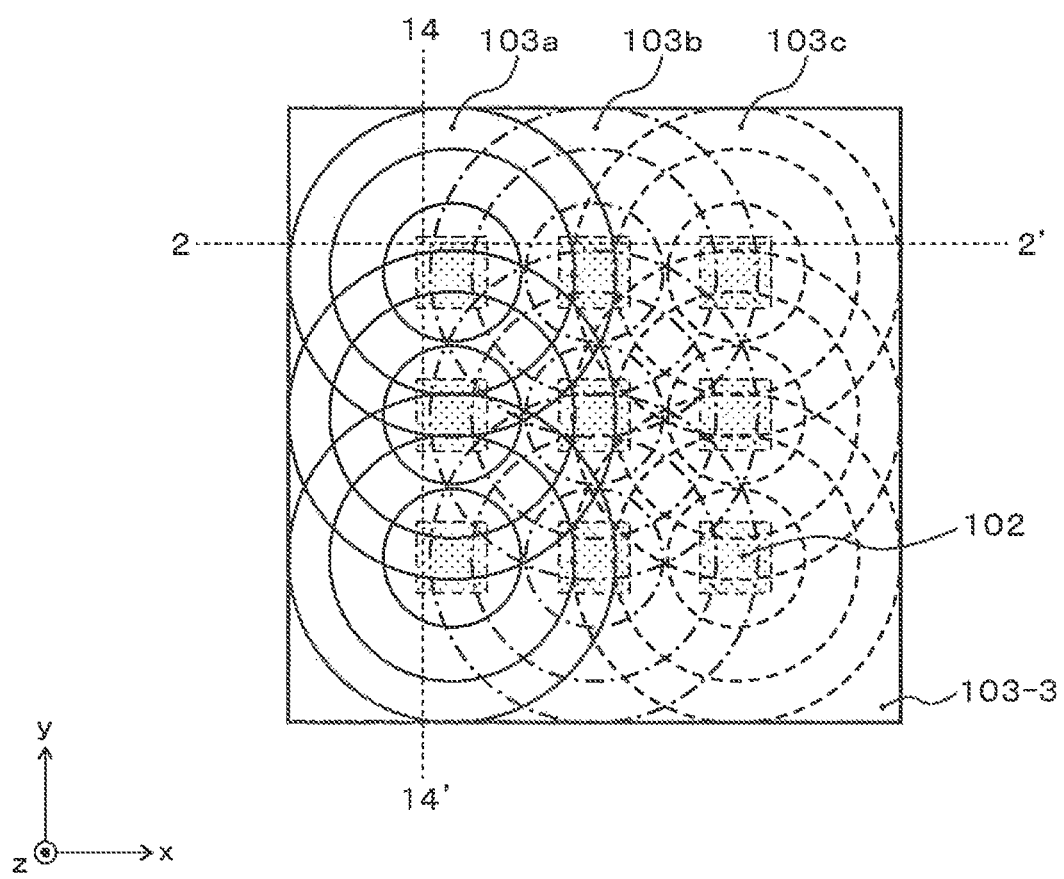
Figure 14:
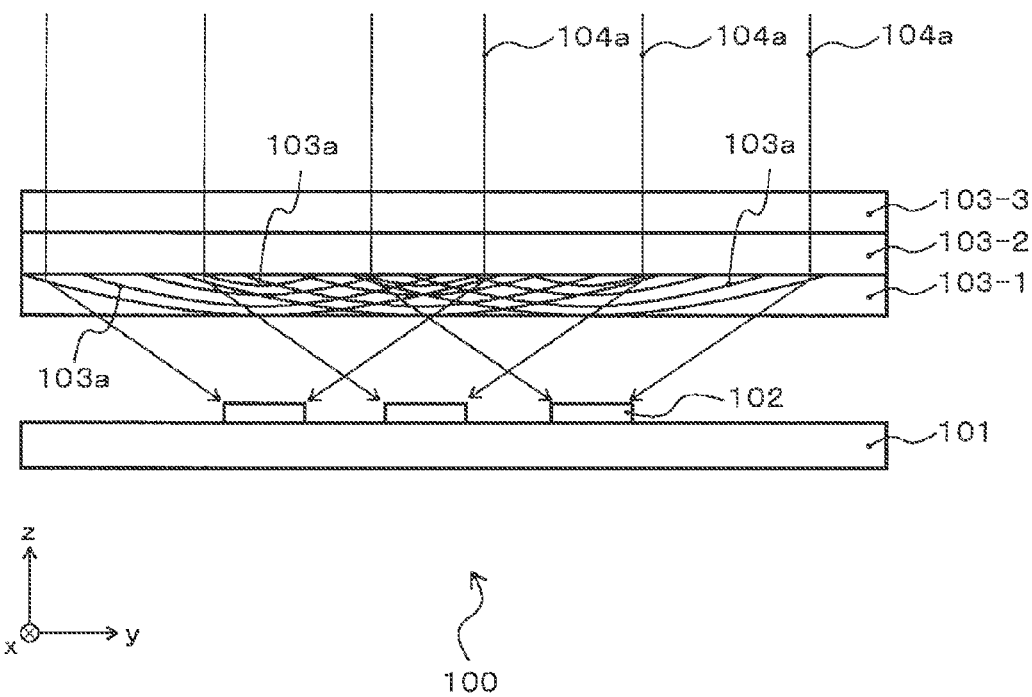

FIG. 3 is an xy plan view of the optical sensor 100 shown in FIG. 1, where first to third diffraction means 103a to 103c formed in the diffraction grating layer structure 103 are illustrated. FIG. 2 is an xz cross-sectional view of the optical sensor 100 taken on line 2-2' of FIG. 3. FIG. 14 is a yz cross-sectional view of the optical sensor 100 taken on line 14-14' of FIG. 3. The first to third diffraction means 103a to 103c illustrated in the drawings are holograms, whose interference fringes are shown there.

The substrate 101 is made of, for example, a metal material (examples: aluminum alloy, copper alloy, iron, iron family alloy, titanium, titanium alloy, or the like), a resin material (examples: epoxy, acrylic, polyimide, polycarbonate, or the like) and a ceramic material (examples: alumina, silica, magnesia, their compounds and complexes, or the like), or the like. The substrate material may be appropriately selected and used according to the usage environment. There is no particular restriction on the planar shape of the substrate 101.

The light receiving parts 102 are each composed of a pyroelectric ceramic film having two principal surfaces and electrode layers formed on the principal surfaces of the pyroelectric ceramic film (neither is illustrated in the drawing). When the pyroelectric ceramic films are irradiated by light, surface charges due to the pyroelectric effect are induced on the electrode surfaces in accordance with the irradiation amount and wavelength of the light. Detection of the light is performed by measuring the induced charges as an electrical signal by the use of an appropriate electrical circuit.

The material of the pyroelectric ceramic film is, for example, a lead zirconate titanate family ceramic, a lithium tantalate family ceramic, or an organic pyroelectric material such as polyvinylidene fluoride. Among these ones, for example, the material of the pyroelectric ceramic film is preferably a lead zirconate titanate family ceramic, which has a high pyroelectric coefficient and whose pyroelectric effect can be derived to the maximum by applying a polarization process. However, the material of the pyroelectric ceramic film is not limited to the pyroelectric materials described above.

The material for the light receiving parts 102 is not limited to pyroelectric materials, but may be any other material having a physical property capable of being changed by the energy of incident light. Examples of a light receiving part 12 using such other materials having a physical property changed by the energy of incident light include a resistance-change type one, which uses the resistance change rate of a material with temperature, and another type one which uses change in electrical characteristics of a semiconductor p-n junction.

The overall size of the light receiving parts 102, in the plan view, needs only to be smaller than that of the substrate 101. Except for this condition, there is no particular restriction on the form of the light receiving parts 102. For example, the thickness of the light receiving parts 102 is preferably between 1 μm and 100 μm.

While nine light receiving parts 102 are arranged in the illustrated example, the number is not limited to nine.

By the way, it is necessary to provide electrical connection between the substrate 101 and the light receiving parts 102. In case that electrical conductivity between the substrate 101 and the light receiving parts 102 is low, wirings need to be formed between the substrate 101 and the light receiving parts 102. The wirings may be formed using, for example, metal wirings by a plating method. For connecting the top electrode layer of the pyroelectric film with the electrical wirings, a wire bonding method also can be used, as well as a plating method.

A gap may be provided between the substrate 101 and the light receiving parts 102. The gap reduces the thermal capacity of a region between the substrate 101 and the light receiving parts 102, thereby increasing the sensitivity. As an example of a substance filling the gap, air or a material having a smaller thermal capacity than that of the substrate 102 is considered.

The diffraction grating layer structure 103 has a configuration in which a first diffraction grating layer 103-1, a second diffraction grating layer 103-2 and a third diffraction grating layer 103-3 are stacked in this order. The diffraction grating layer structure 103 may have a configuration in which a larger number of diffraction grating layers are stacked, or may consist of only a single diffraction grating layer or two diffraction grating layers. Examples with a diffraction grating layer structure 103 consisting of one or two diffraction grating layers will be described in later exemplary embodiments.

In the first diffraction grating layer 103-1, a plurality of first diffraction means 103a for diffracting and thereby condensing light of a first wavelength are formed. Then, as shown in FIGS. 3 and 14, at least some of the plurality of first diffraction means 103a formed in the first diffraction grating layer 103-1 each overlap at least partly with other ones of the plurality of first diffraction means 103a neighboring it in the y-direction.

In the second diffraction grating layer 103-2, a plurality of second diffraction means 103b for diffracting and thereby condensing light of a second wavelength, which is different from the first wavelength, are formed. Then, as shown in FIGS. 2 and 3, in the plan view, at least some of the plurality of first diffraction means 103a formed in the first diffraction grating layer 103-1 each overlap at least partly with some of the second diffraction means 103b formed in the second diffraction grating layer 103-2. Further, as shown in FIG. 3, at least some of the plurality of second diffraction means 103b formed in the second diffraction grating layer 103-2 each overlap at least partly with other ones of the plurality of second diffraction means 103b neighboring it in the y-direction.

In the third diffraction grating layer 103-3, a plurality of third diffraction means 103c for diffracting and thereby condensing light of a third wavelength, which is different from both of the first and second wavelengths, are formed. Then, as shown in FIGS. 2 and 3, in the plan view, at least some of the plurality of second diffraction means 103b formed in the second diffraction grating layer 103-2 each overlap at least partly with some of the third diffraction means 103c formed in the third diffraction grating layer 103-3. Further, as shown in FIG. 3, at least some of the plurality of third diffraction means 103c formed in the third diffraction grating layer 103-3 each overlap at least partly with other ones of the plurality of third diffraction means 103c neighboring it in the y-direction. Here, in the plan view, at least some of the plurality of first diffraction means 103a formed in the first diffraction grating layer 103-1 may each overlap at least partly with some of the third diffraction means 103c formed in the third diffraction grating layer 103-3.

The diffraction grating layer structure 103 is made of a hologram material into which intensity distribution according to the wavelength of incident light is to be recorded in the form of refractive index distribution. For example, the hologram material is a photopolymer.

Figure 4:
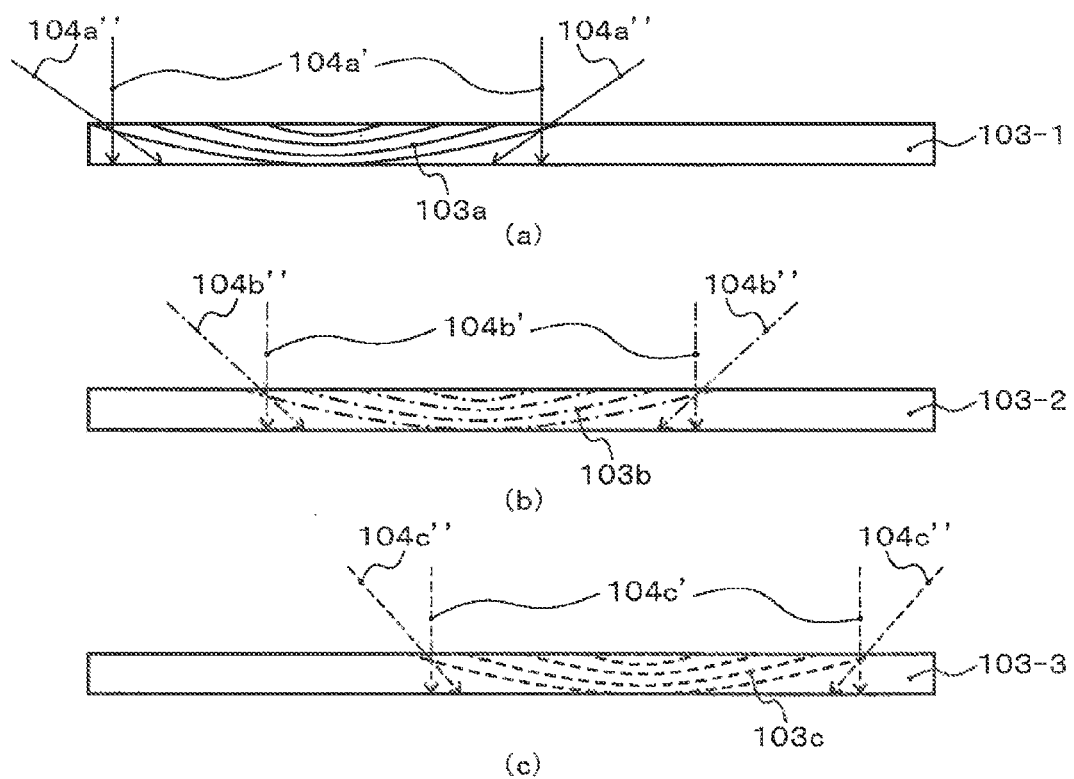

FIG. 4 is a diagram showing a fabrication method of the first to third diffraction grating layers 103-1 to 103-3, where the first to third diffraction grating layers 103-1 to 103-3 are illustrated in a separated manner in an xz cross-sectional view.

The first diffraction means 103a may be fabricated by the following method. As shown in FIG. 4 (a), a hologram material is irradiated by both reference light 104a', which is collimated light emitted from a laser, and signal light 104a", which is condensed light obtained by condensing light emitted from a laser by the use of an optical element such as a lens. Each of the reference light 104a' and the signal light 104a" is light of a wavelength a (the first wavelength). In an area thus irradiated, within the hologram material, interference fringes according to both intensity distribution of the reference light 104a' and that of the signal light 104a" are generated. In the irradiated area, molecules of the hologram material are caused to move by the light intensity distribution, and accordingly, a diffraction grating (the first diffraction means 103a) is recorded in the form of a refractive index distribution. For some kind of hologram material, post processing (bleaching) for immobilizing the molecules may be performed after the recording.

The second diffraction means 103b may be fabricated by the following method. As shown in FIG. 4 (b), a hologram material is irradiated by both reference light 104b', which is collimated light emitted from a laser, and signal light 104b", which is condensed light obtained by condensing light emitted from a laser by the use of an optical element such as a lens. Each of the reference light 104b' and the signal light 104b" is light of a wavelength b (the second wavelength). In an area thus irradiated, within the hologram material, interference fringes according to both intensity distribution of the reference light 104b' and that of the signal light 104b" are generated. In the irradiated area, molecules of the hologram material are caused to move by the light intensity distribution, and accordingly, a diffraction grating (the second diffraction means 103b) is recorded in the form of a refractive index distribution. For some kind of hologram material, post processing (bleaching) for immobilizing the molecules may be performed after the recording.

The third diffraction means 103c may be fabricated by the following method. As shown in FIG. 4 (*c*), a hologram material is irradiated by both reference light 104c', which is collimated light emitted from a laser, and signal light 104c", which is condensed light obtained by condensing light emitted from a laser by the use of an optical element such as a lens. Each of the reference light 104c' and the signal light 104c" is light of a wavelength c (the third wavelength). In an area thus irradiated, within the hologram material, interference fringes according to both intensity distribution of the reference light 104c' and that of the signal light 104c" are generated. In the irradiated area, molecules of the hologram material are caused to move by the light intensity distribution, and accordingly, a diffraction grating (the third diffraction means 103b) is recorded in the form of a refractive index distribution. For some kind of hologram material, post processing (bleaching) for immobilizing the molecules may be performed after the recording.

Here, the holograms may be produced using a material into which polarization distribution of incident light is recorded in the form of molecule orientation distribution.

Next, using FIGS. 2 and 14, a description will be given of operation and effect of the optical sensor 100 of the present exemplary embodiment.

Out of light projected onto the optical sensor 100 from a light source (not illustrated in the drawings) located in a top region of the drawings, light of the wavelength a (the first wavelength) becomes incident on the first diffraction grating layer 103-1 after passing through the third diffraction grating layer 103-3 and the second diffraction grating layer 103-2 in this order. Out of the light of the wavelength a (the first wavelength) incident on the first diffraction grating layer 103-1, incident light 104a having entered the first diffraction means 103a is diffracted by the first diffraction means 103a, thereby being condensed at a corresponding one of the light receiving parts 102. Out of the light of the wavelength a (the first wavelength) incident on the first diffraction grating layer 103-1, light not entering the first diffraction means 103a passes through the first diffraction grating layer 103-1.

Out of the light projected onto the optical sensor 100 from the light source (not illustrated in the drawings) located in the top region of the drawings, light of the wavelength b (the second wavelength) becomes incident on the second diffraction grating layer 103-2 after passing through the third diffraction grating layer 103-3. Out of the light of the wavelength b (the second wavelength) incident on the second diffraction grating layer 103-2, incident light 104b having entered the second diffraction means 103b is diffracted by the second diffraction means 103b, thereby being condensed at a corresponding one of the light receiving parts 102 after passing through the first diffraction grating layer 103-1. Out of the light of the wavelength b (the second wavelength) incident on the second diffraction grating layer 103-2, light not entering the second diffraction means 103b passes through the second diffraction grating layer 103-2 and subsequently through the first diffraction grating layer 103-1.

Out of light of the wavelength c (the third wavelength) incident on the third diffraction grating layer 103-3 after being projected onto the optical sensor 100 from the light source (not illustrated in the drawings) located in the top region of the drawings, incident light 104c having entered the third diffraction means 103c is diffracted by the third diffraction means 103c. Then, the incident light 104c is condensed at a corresponding one of the light receiving parts 102 after passing through the second diffraction grating layer 103-2 and the first diffraction grating layer 103-1 in this order. Out of the light of the wavelength c (the third wavelength) incident on the third diffraction grating layer 103-3, light not entering the third diffraction means 103c passes through the third diffraction grating layer 103-3, and subsequently through the second diffraction grating layer 103-2 and the first diffraction grating layer 103-1 in this order.

Out of the light projected onto the optical sensor 100 from the light source (not illustrated in the drawings) located in the top region of the drawings, light of other wavelengths than the wavelength a (the first wavelength), the wavelength b (the second wavelength) nor the wavelength c (the third wavelength) passes through the third diffraction grating layer 103-3, the second diffraction grating layer 103-2 and the first diffraction grating layer 103-1 in this order.

From a total sum, with respect to each of the incident light components 104a, 104b and 104c, of output voltages generated by incidence of light on corresponding ones of the light receiving parts 102, the amount of received light may be calculated with respect to each of light of the wavelength a (the first wavelength), that of the wavelength b (the second wavelength) and that of the wavelength c (the third wavelength).

As has been described above, according to the optical sensor 100 of the present exemplary embodiment, incident light spreading out in the x- and y-directions can be efficiently condensed at the light receiving parts 102. As a result, the amount of received light at the light receiving parts 102 is increased, and it accordingly becomes possible to increase the sensitivity of the sensor 100.

The optical sensor 100 of the present exemplary embodiment realizes a configuration in which a plurality of diffraction means located in the same layer are each constituted by a hologram, where mutually neighboring ones of the diffraction means overlap at least partly with each other. Therefore, such diffraction means overlapping at least partly with each other can be fabricated relatively easily. In that case, the configuration does not become large in the thickness direction of the substrate, and accordingly contributes to size reduction of the optical sensor 100.

Second Exemplary Embodiment

Figure 5:
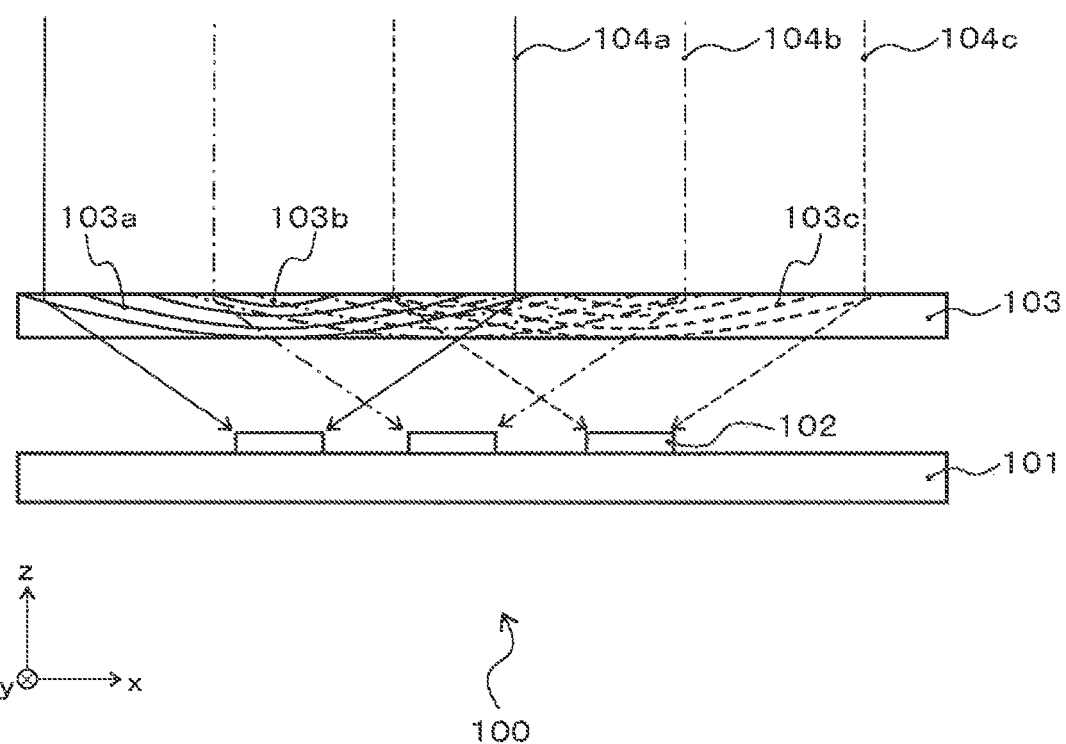

A perspective view of an optical sensor 100 of the present exemplary embodiment is shown by FIG. 1, and its plan view by FIG. 3. FIG. 5 is an xz cross-sectional view of the optical sensor 100 of the present exemplary embodiment. The cross-sectional view is that taken on line 2-2' of FIG. 3.

A diffraction grating layer structure 103 of the present exemplary embodiment is composed of only a single layer in which first to third diffraction means 103a to 103c are formed together. The first to third diffraction means 103a to 103c of the present exemplary embodiment are each constituted by a hologram. There, diffraction means neighboring each other in the x-direction overlap at least partly with each other.

Figure 6:
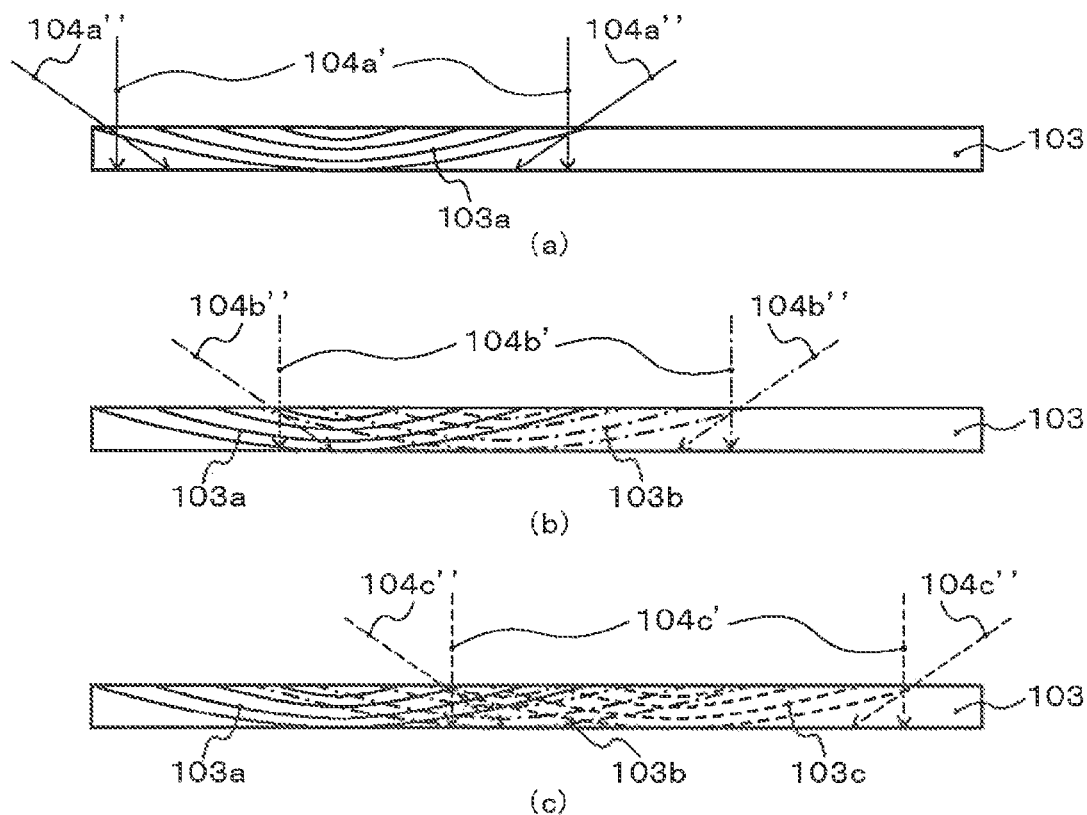

FIG. 6 is a diagram showing an xz cross-sectional view of the diffraction grating layer structure 103, where a fabrication method of each of the first to third diffraction means 103a to 103c is shown.

The first diffraction means 103a may be fabricated by the following method. As shown in FIG. 6 (a), a hologram material is irradiated by both reference light 104a', which is collimated light emitted from a laser, and signal light 104a", which is condensed light obtained by condensing light emitted from a laser by the use of an optical element such as a lens. Each of the reference light 104a' and the signal light 104a" is light of the wavelength a (the first wavelength). In an area thus irradiated, within the hologram material, interference fringes according to both intensity distribution of the reference light 104a' and that of the signal light 104a" are generated. In the irradiated area, molecules of the hologram material are caused to move by the light intensity distribution, and accordingly, a diffraction grating (the first diffraction means 103a) is recorded in the form of a refractive index distribution.

The second diffraction means 103b may be fabricated by the following method. As shown in FIG. 6 (b), the hologram material is irradiated by both reference light 104b', which is collimated light emitted from a laser, and signal light 104b", which is condensed light obtained by condensing light emitted from a laser by the use of an optical element such as a lens. Each of the reference light 104b' and the signal light 104b" is light of the wavelength b (the second wavelength). In an area thus irradiated, within the hologram material, interference fringes according to both intensity distribution of the reference light 104b' and that of the signal light 104b" are generated. In the irradiated area, molecules of the hologram material are caused to move by the light intensity distribution, and accordingly, a diffraction grating (the second diffraction means 103a) is recorded in the form of a refractive index distribution.

The third diffraction means 103c may be fabricated by the following method. As shown in FIG. 6 (c), the hologram material is irradiated by both reference light 104c', which is collimated light emitted from a laser, and signal light 104c", which is condensed light obtained by condensing light emitted from a laser by the use of an optical element such as a lens. Each of the reference light 104c' and the signal light 104c" is light of the wavelength c (the third wavelength). In an area thus irradiated, within the hologram material, interference fringes according to both intensity distribution of the reference light 104c' and that of the signal light 104c" are generated. In the irradiated area, molecules of the hologram material are caused to move by the light intensity distribution, and accordingly, a diffraction grating (the third diffraction means 103c) is recorded in the form of a refractive index distribution.

The first to third diffraction means 103a to 103c can be fabricated by sequentially performing the above-described processes on a single hologram material, as shown in the diagram. For some kind of hologram material, post processing (bleaching) for immobilizing the molecules may be performed after recording the first to third diffraction means 103a to 103c.

The optical sensor 100 of the present exemplary embodiment can be fabricated with its thickness in the z-direction being smaller than that of the optical sensor 100 of the first exemplary embodiment, and accordingly can be made smaller in size. Here, the holograms may be produced using a material into which polarization distribution of incident light is recorded in the form of molecule orientation distribution.

Third Exemplary Embodiment

Figure 7:
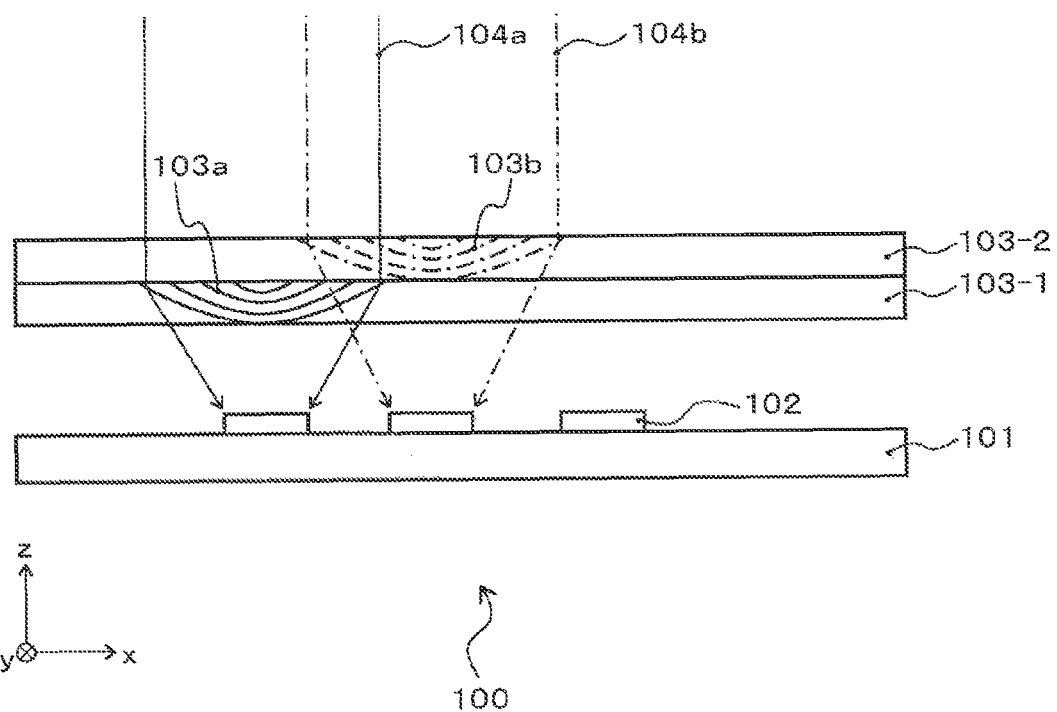

A perspective view of an optical sensor 100 of the present exemplary embodiment is shown by FIG. 1. Its plan view corresponds to that obtained by removing the third diffraction means 103c from FIG. 3. FIG. 7 is an xz cross-sectional view of the optical sensor 100 of the present exemplary embodiment. The cross-sectional view is that taken on line 2-2' of the plan view obtained by removing the third diffraction means 103c from FIG. 3. Compared to the optical sensor 100 of FIG. 2, there is a difference in not comprising the third diffraction grating layer 103-3.

Both the first and second exemplary embodiments have a configuration in which all of the plurality of light receiving parts 102 have respectively corresponding diffraction means, and light of a predetermined wavelength diffracted by each of the diffraction means is condensed at the corresponding one of the light receiving parts 102. The present exemplary embodiment is different from the first and second exemplary embodiments in that at least one of the plurality of light receiving parts 102 has no corresponding diffraction means. In the case of the example shown in FIG. 7, a diffraction means corresponding to the light receiving part 102 located at the left end is the first diffraction means 103a, and that corresponding to the center light receiving part 102 is the second diffraction means 103b. Then, there exists no diffraction means corresponding to the light receiving part 102 located at the right end.

While the example shown in FIG. 7 has a configuration based on that of the first exemplary embodiment, an optical sensor 100 of the present exemplary embodiment having the above-described features may also be configured on the basis of the configuration of the second exemplary embodiment.

According to the present exemplary embodiment thus configured, as in FIG. 7, it is possible to correct data detected by each of the light receiving parts 102 having respectively corresponding diffraction means, by the use of data detected by the light receiving part 102 not having a corresponding diffraction means.

Data detected by each of the light receiving parts 102 having respectively corresponding diffraction means is that resulting from light having entered the light receiving part 102 after being diffracted by the corresponding diffraction means at a wavelength-dependent efficiency and angle. While data detected by each of the light receiving parts 102 is caused to change by a change in temperature or the optical path length, or the like, it may also be caused to change by a change in the corresponding diffraction means. For this reason, when there has occurred a change of data detected by any of the light receiving parts 102 having respectively corresponding diffraction means, it is impossible to determine whether the change is caused by a change in temperature or the optical path length, or the like, or is caused by the corresponding diffraction means.

In the optical sensor 100 of the present exemplary embodiment, there exists the light receiving part 102 not having a corresponding diffraction means. Accordingly, by referring to data detected by the light receiving part 102 not having a corresponding diffraction means, it is possible to determine whether a change of data detected by any the light receiving parts 102 having respectively corresponding diffraction means has been caused by a change in temperature or the optical path length, or the like, or caused by the corresponding diffraction means. Then, if it is determined that the change of data detected by the light receiving part 102 having a corresponding diffraction means has been caused by a change in temperature or the optical path length, or the like, correction can be made appropriately in terms of temperature dependence of the light receiving part 102 or its dependence on the optical path length between itself and the light source.

Fourth Exemplary Embodiment

Figure 8:
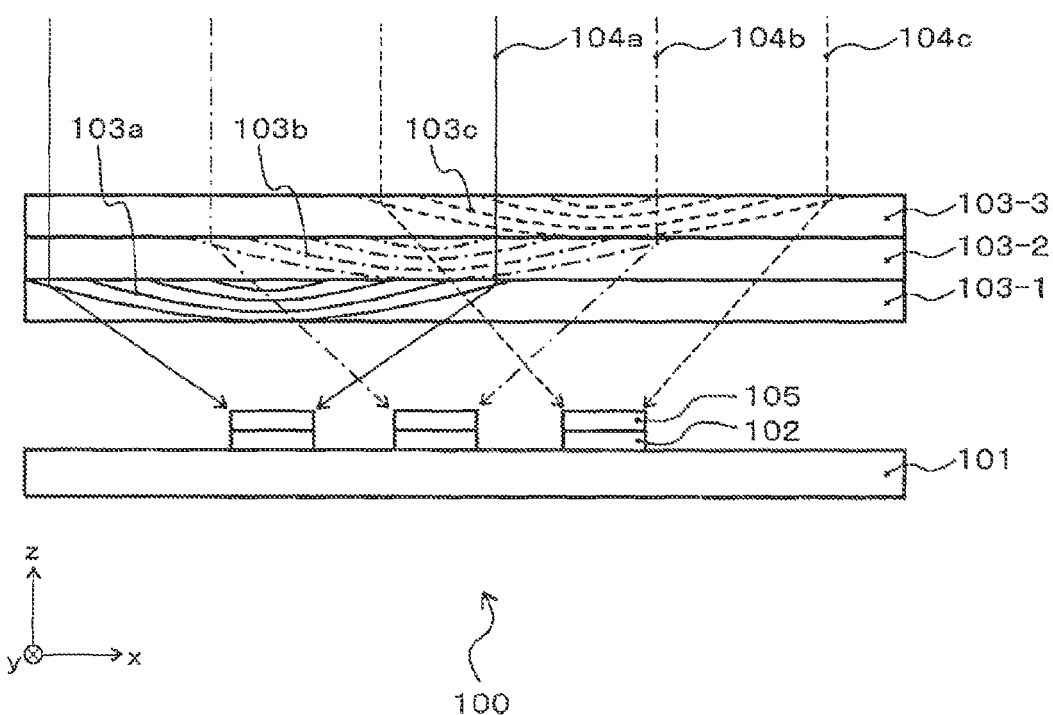

A perspective view of an optical sensor 100 of the present exemplary embodiment corresponds to that obtained by arranging a filter 105 (not illustrated) on each of the light receiving parts 102 in FIG. 1. Its plan view corresponds to that obtained by arranging the filters 105 (not illustrated in FIG. 3) on respective ones of the light receiving parts 102 in FIG. 3. FIG. 8 is an xz cross-sectional view of the optical sensor 100 of the present exemplary embodiment. The cross-sectional view is that taken on line 2-2' of the plan view obtained by arranging the filters 105 (not illustrated in FIG. 3) on respective ones of the light receiving parts 102 in FIG. 3. As shown in FIG. 8, on each of the light receiving parts 102, a filter 105 for cutting off light except for that of a specific wavelength is arranged. For example, the filters 105 are each a dichroic filter formed of a dielectric multilayer.

Referring to FIG. 8, on the light receiving part 102 corresponding to the first diffraction means 103a for diffracting light of the wavelength a (the first wavelength), a filter 105 for transmitting light of the wavelength a (the first wavelength) but cutting off light of other wavelengths is arranged. On the light receiving part 102 corresponding to the second diffraction means 103b for diffracting light of the wavelength b (the second wavelength), a filter 105 for transmitting light of the wavelength b (the second wavelength) but cutting off light of other wavelengths is arranged. On the light receiving part 102 corresponding to the third diffraction means 103c for diffracting light of the wavelength c (the third wavelength), a filter 105 for transmitting light of the wavelength c (the third wavelength) but cutting off light of other wavelengths is arranged.

According to the optical sensor 100 of the present exemplary embodiment, noise can be reduced as a result of cutting off light other than that of a desired wavelength by the use of the filters 105.

While the example shown in FIG. 8 has a configuration based on that of the first exemplary embodiment, an optical sensor 100 of the present exemplary embodiment having the above-described features may also be configured on the basis of the configuration of the second or third exemplary embodiments. Also in that way, the above-described operation and effect can be realized.

Fifth Exemplary Embodiment

Figure 9:
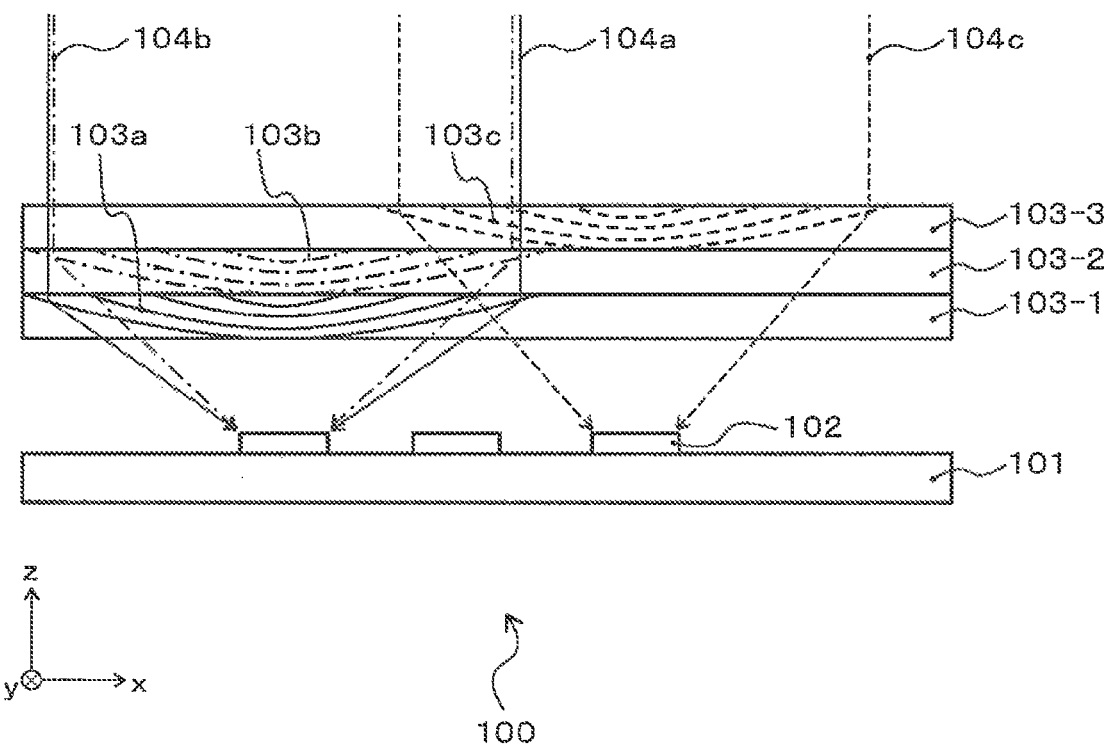

A perspective view of an optical sensor 100 of the present exemplary embodiment is shown by FIG. 1. Its plan view corresponds to that obtained from FIG. 3 by shifting the location of the second diffraction means 103b toward the side of the first diffraction means 103a, thereby making the first diffraction means 103a and the second diffraction means 103b almost completely overlap with each other. FIG. 9 is an xz cross-sectional view of the optical sensor 100 of the present exemplary embodiment. The cross-sectional view is that taken on line 2-2' of the diagram obtained from FIG. 3 by shifting the location of the second diffraction means 103b toward the side of the first diffraction means 103a and thereby making the first diffraction means 103a and the second diffraction means 103b almost completely overlap with each other.

According to the optical sensor 100 of the present exemplary embodiment, both the first incident light 104a and the second incident light 104b are condensed at the same one of the light receiving parts 102. By thus condensing both the first incident light 104a and the second incident light 104b at the same one of the light receiving parts 102, for example, when measuring light of a wide wavelength range instead of measuring only light of a specific wavelength, it is possible to increase the amount of received light at the light receiving part and thereby increase the sensitivity, without increasing the number of light receiving parts.

While the example shown in FIG. 9 has a configuration based on that of the first exemplary embodiment, an optical sensor 100 of the present exemplary embodiment having the above-described features may also be configured on the basis of the configuration of any one of the second to fourth exemplary embodiments. Also in that way, the above-described operation and effect can be realized.

Sixth Exemplary Embodiment

Figure 10:
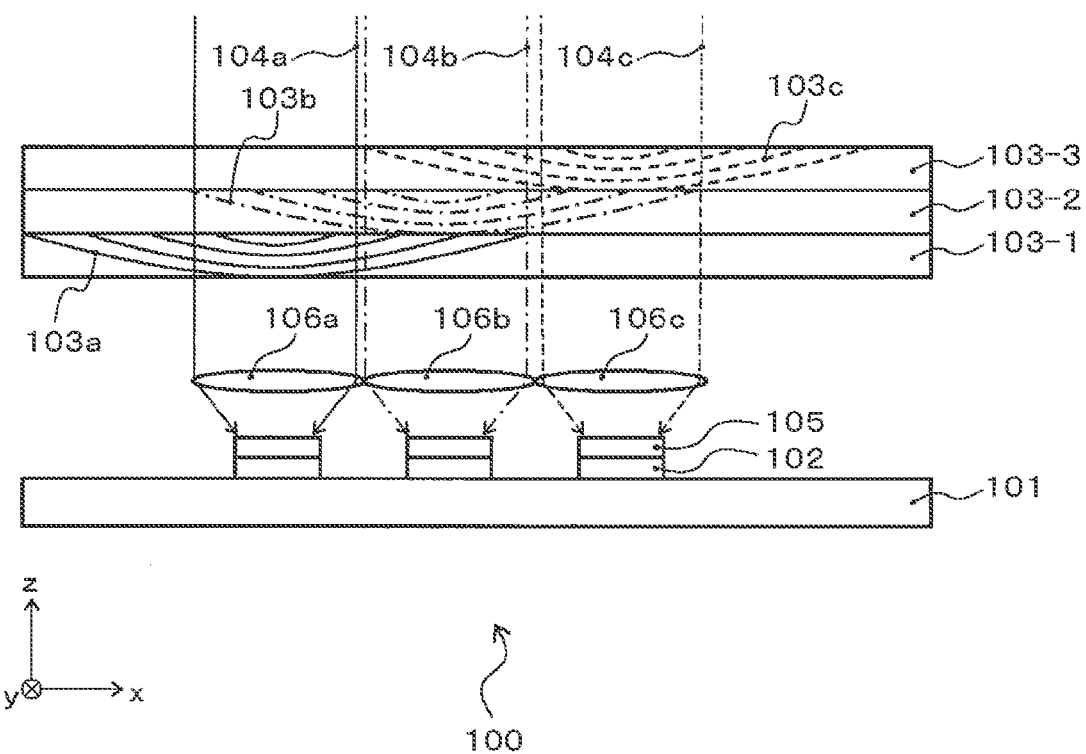

A perspective view of an optical sensor 100 of the present exemplary embodiment corresponds to that obtained from FIG. 1 by arranging a filter 105 (not illustrated in FIG. 1) on each of the light receiving parts 102 and further arranging one of lenses 106a to 106c (not illustrated in FIG. 1) between the filter 105 and the diffraction grating layer structure 103. Its plan view corresponds to that obtained from FIG. 3 by arranging the filters 105 (not illustrated in FIG. 3) on respective ones of the light receiving parts 102 and further arranging one of the lenses 106a to 106c (not illustrated in FIG. 3) between each of the filters 105 and the diffraction grating layer structure 103. FIG. 10 is an xz cross-sectional view of the optical sensor 100 of the present exemplary embodiment. The cross-sectional view is that taken on line 2-2' of the plan view obtained from FIG. 3 by arranging the filters 105 (not illustrated in FIG. 3) on respective ones of the light receiving parts 102 and further arranging one of the lenses 106a to 106c (not illustrated in FIG. 3) between each of the filters 105 and the diffraction grating layer structure 103.

As shown in FIG. 10, on each of the light receiving parts 102, a filter 105 for cutting off light except for that of a specific wavelength is arranged. For example, the filters 105 are each a dichroic filter formed of a dielectric multilayer. Between each of the light receiving parts 102 and the diffraction grating layer structure 103 (the corresponding diffraction means), an optical system for condensing incident light (any one of the lenses 106a to 106c) is arranged. The material of the lenses 106a to 106c is, for example, an optical glass such as BK-7 or a resin such as acrylic when the wavelength of incident light is in the visible region. When the wavelength of incident light is in the infrared region, the material of the lenses 106a to 106c is, for example, Si, high-density polyethylene or germanium. The lenses 106a to 106c are arranged in a manner to be correlated to respective ones of the light receiving parts 102.

Referring to FIG. 10, the lens 106a condenses, out of the incident light 104a, light having passed through, without being diffracted by, the first diffraction means 103a at the filter 105 arranged on the light receiving part 102 corresponding to the first diffraction means 103a. The light condensed at the filter 105 passes through the filter 105 and becomes incident on the light receiving part 102.

The lens 106b condenses, out of the incident light 104b, light having passed through, without being diffracted by, the second diffraction means 103b at the filter 105 arranged on the light receiving part 102 corresponding to the second diffraction means 103b. The light condensed at the filter 105 passes through the filter 105 and becomes incident on the light receiving part 102.

The lens 106c condenses, out of the incident light 104c, light having passed through, without being diffracted by, the third diffraction means 103c at the filter 105 arranged on the light receiving part 102 corresponding to the third diffraction means 103c. The light condensed at the filter 105 passes through the filter 105 and becomes incident on the light receiving part 102.

According to the present exemplary embodiment, by thus condensing light components having passed, without being diffracted by, the first to third diffraction means 103a to 103c at the light receiving parts 102, by means of the lenses 106a to 106c, it is possible to increase the amount of received light at the light receiving parts 102 and accordingly to increase their sensitivity.

In a modified example of the present exemplary embodiment, optical systems (lenses) for condensing incident light may be provided on the opposite side, across the diffraction grating layer structure 103, to the substrate 101 and the light receiving parts 102 (in an area above the diffraction grating layer 103-3, in FIG. 10), in addition to or in place of the lenses 106a to 106c. The optical systems may be arranged in a manner to be correlated to respective ones of the light receiving parts 102. By thus configuring, the light condensation efficiency at the light receiving parts 102 can be further improved.

In another modified example of the present exemplary embodiment, optical systems (lenses) for collimating incident light may be provided on the opposite side, across the diffraction grating layer structure 103, to the substrate 101 and the light receiving parts 102 (in an area above the diffraction grating layer 103-3, in FIG. 10), in addition to or in place of the lenses 106a to 106c. In a hologram (diffraction means) formed by the use of collimated light, the diffraction efficiency is high on collimated light identical to the formation light. In the case of being provided with the optical systems (lenses) for collimating incident light, it becomes possible to have incident light being efficiently incident on the holograms (diffraction means) and efficiently diffracted by the holograms (diffraction means).

While the example shown in FIG. 10 has a configuration based on that of the first exemplary embodiment, an optical sensor 100 of the present exemplary embodiment having the above-described features may also be configured on the basis of the configuration of any one of the second to fifth exemplary embodiments. Also in that way, the above-described operation and effect can be realized.

Seventh Exemplary Embodiment

Figure 11:
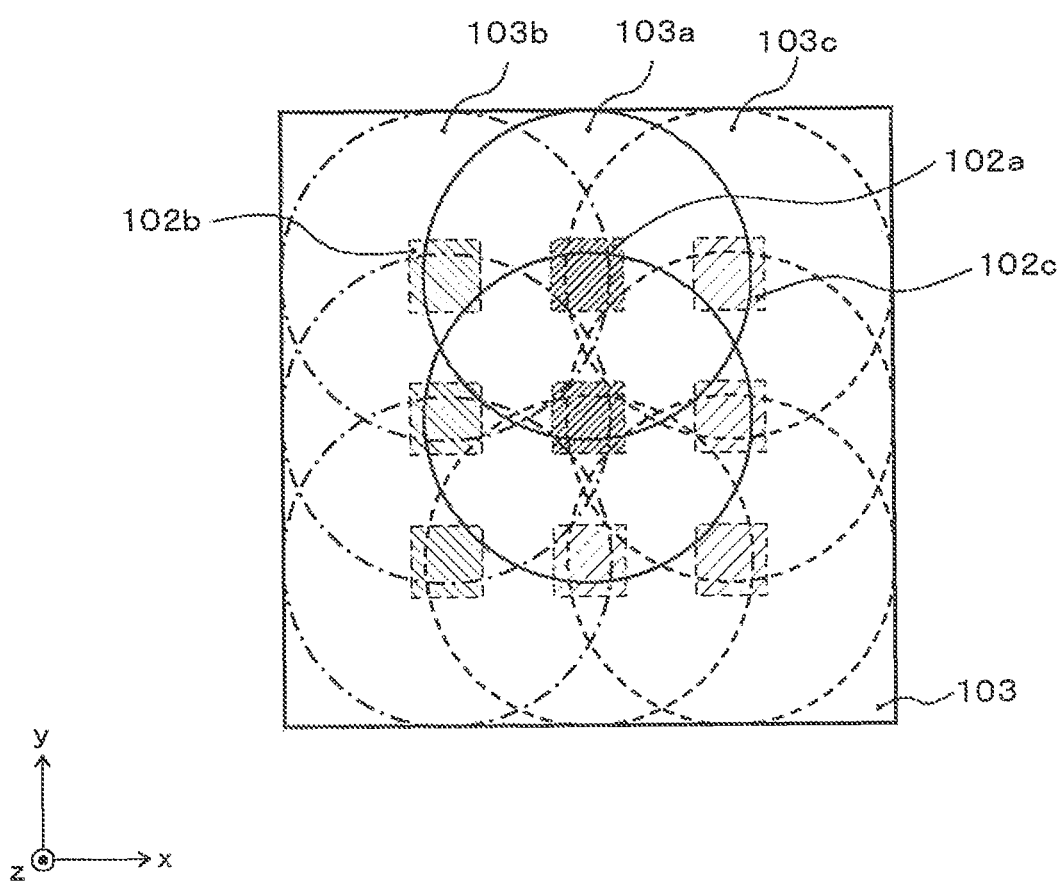

A perspective view of an optical sensor 100 of the present exemplary embodiment is shown by FIG. 1. FIG. 11 is an xy plan view of the optical sensor 100 shown by FIG. 1, where the first to third diffraction means 103a to 103c formed in the diffraction grating layer structure 103 are illustrated. Compared to the first to sixth exemplary embodiments, where the numbers of first to third diffraction means 103a to 103c are coincident with each other, the present exemplary embodiment is different in that the numbers of first to third diffraction means 103a to 103c are not coincident with each other.

In the case of the example shown in FIG. 11, the number of first diffraction means 103a is two, that of second diffraction means 103b is three, and that of third diffraction means 103c is four.

Here, the sensitivity to light of the wavelength a (the first wavelength) of the light receiving parts 102a corresponding to the first diffraction means 103a for diffracting light of the wavelength a (the first wavelength) is represented by Ca, the sensitivity to light of the wavelength b (the second wavelength) of the light receiving parts 102b corresponding to the second diffraction means 103b for diffracting light of the wavelength b (the second wavelength) is represented by Cb, and the sensitivity to light of the wavelength c (the third wavelength) of the light receiving parts 102c corresponding to the third diffraction means 103c for diffracting light of the wavelength c (the third wavelength) is represented by Cc.

In the present exemplary embodiment, a relation Ca>Cb>Cc stands. In that case, as shown in FIG. 11, the relation among the numbers of the first to third diffraction means 103a to 103c is determined to be: the first diffraction means 103a<the second diffraction means 103b<the third diffraction means 103c.

In the present exemplary embodiment, the plurality of light receiving parts 102 include the light receiving parts 102a to 102c for detecting light of different wavelengths, and they are accordingly divided into a plurality of groups in terms of the wavelength of light to be detected. That is, they are divided into a group of the light receiving parts 102a for detecting light of the wavelength a (the first wavelength), a group of the light receiving parts 102b for detecting light of the wavelength b (the second wavelength), and a group of the light receiving parts 102c for detecting light of the wavelength c (the third wavelength). Then, for a group of light receiving parts 102 having lower sensitivity to light of the target wavelength for their detection, a larger number of diffraction means corresponding to the light receiving parts 102 are provided.

According to the present exemplary embodiment thus configured, the number of diffraction means corresponding to a group of light receiving parts 102 having higher sensitivity to light of the target wavelength for their detection is set to be smaller, and the number of diffraction means corresponding to a group of light receiving parts 102 having lower sensitivity to light of the target wavelength for their detection is set to be larger. By thus configuring, it is possible, with respect to light to which the sensitivity is intrinsically low, to increase its amount to be taken in. As a result, the effective sensitivity to such light can be increased.

An optical sensor 100 of the present exemplary embodiment may be configured on the basis of also the configuration of any one of the first to sixth exemplary embodiments.

Eighth Exemplary Embodiment

Figure 12:
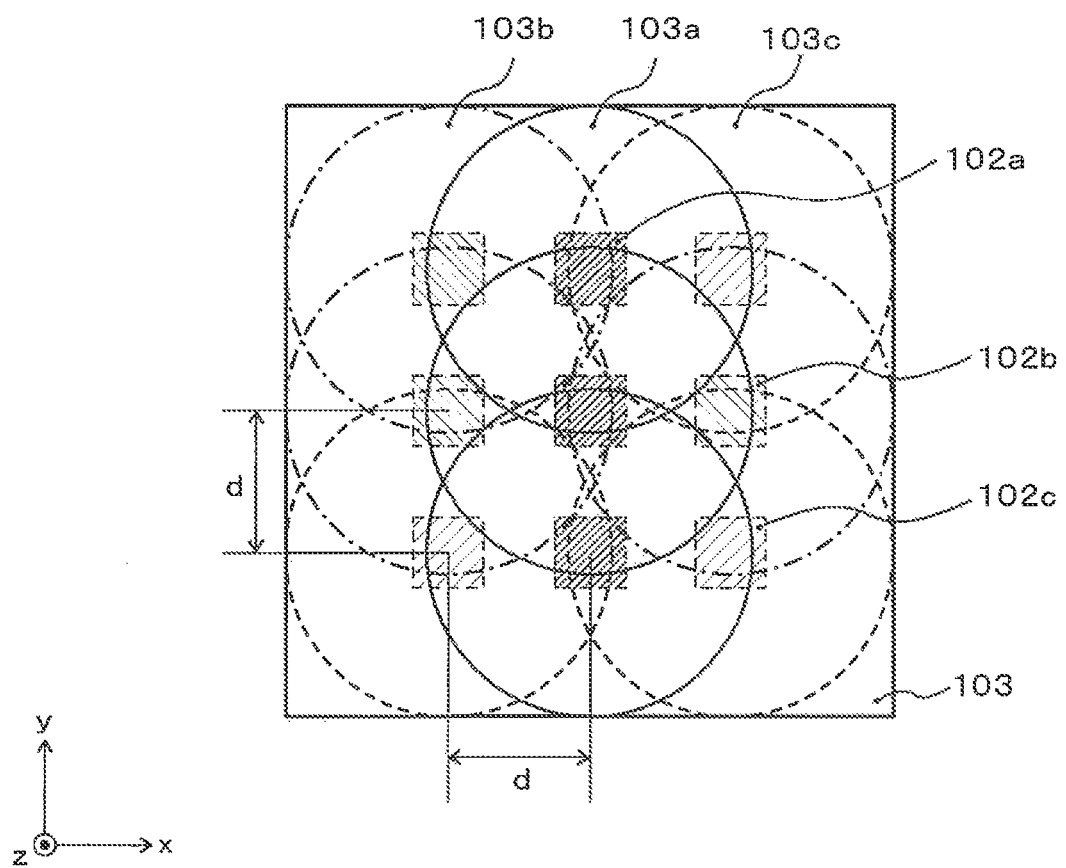

A perspective view of an optical sensor 100 of the present exemplary embodiment is shown by FIG. 1. FIG. 12 is an xy plan view of the optical sensor 100 shown by FIG. 1, where the diffraction means formed in the diffraction grating layer structure 103 are illustrated. Compared to the first to seventh exemplary embodiments, the present exemplary embodiment is different in arrangement of the first to third diffraction means 103a to 103c.

Here, the sensitivity to light of the wavelength a (the first wavelength) of the light receiving parts 102a corresponding to the first diffraction means 103a for diffracting light of the wavelength a (the first wavelength) is represented by Ca, the sensitivity to light of the wavelength b (the second wavelength) of the light receiving parts 102b corresponding to the second diffraction means 103b for diffracting light of the wavelength b (the second wavelength) is represented by Cb, and the sensitivity to light of the wavelength c (the third wavelength) of the light receiving parts 102c corresponding to the third diffraction means 103c for diffracting light of the wavelength c (the third wavelength) is represented by Cc. In the present exemplary embodiment, a relation Ca>Cb>Cc stands.

In the present exemplary embodiment, the plurality of light receiving parts 102 include the light receiving parts 102a to 102c for detecting light of different wavelengths, and they are accordingly divided into a plurality of groups in terms of the wavelength of light to be detected. That is, they are divided into a group of the light receiving parts 102a for detecting light of the wavelength a (the first wavelength), a group of the light receiving parts 102b for detecting light of the wavelength b (the second wavelength), and a group of the light receiving parts 102c for detecting light of the wavelength c (the third wavelength). Then, they are arranged such that, for a group of light receiving parts 102 having lower sensitivity to light of the target wavelength for their detection, the total sum of center-to-center spacings, in the lateral direction perpendicular to the thickness direction of the substrate 101, between diffraction means corresponding to the light receiving parts 102 is larger.

The total sum of center-to-center spacings is obtained, for each of the groups, by creating all possible pairs between the plurality of light receiving parts 102 included in the group, calculating the center-to-center spacing between diffraction means corresponding to a pair of light receiving parts 102, for each and every one of the pairs, and summing up thus calculated center-to-center spacings.

If the total sum of center-to-center spacings between the first diffraction means 103a in FIG. 12 is represented by Da, that of center-to-center spacings between the second diffraction means 103b by Db, and that of center-to-center spacings between the third diffraction means 103c by Dc, then Da, Db and Dc are given by equations 1, 2 and 3, respectively. Here, d represents a center-to-center spacing between diffraction means neighboring each other in the x- or y-direction.

$$D_a = 4d \quad (1)$$

$$D_b = 2d + d + \sqrt{(2d)^2 + (d)^2} = (3 + \sqrt{5})d \quad (2)$$

$$D_c = 2d - 2d + \sqrt{(2d)^2 + (2d)^2} = (4 + 2\sqrt{2})d \quad (3)$$

From the equations (1), (2) and (3), Da<Db<Dc is noticed. That is, the arrangement in FIG. 12 is made such that, for a group of light receiving parts 102 having lower sensitivity to light of the target wavelength for their detection, the total sum of center-to-center spacings, in the lateral direction perpendicular to the thickness direction of the substrate 101, between diffraction means corresponding to the light receiving parts 102 is larger.

By thus setting to be larger the center-to-center spacing between diffraction means corresponding to light receiving parts 102 having lower sensitivity at the target wavelength of their detection, an overlapping area between diffraction means for diffracting light of the same wavelength is reduced. As a result, with respect to light of a wavelength to which the sensitivity is low, its amount to be taken in is increased, its amount to be diffracted and thereby condensed at the corresponding light receiving parts 102 is accordingly increased, and thereby, the sensitivity to it can be increased.

An optical sensor 100 of the present exemplary embodiment can be configured also on the basis of the configuration of any one of the first to seventh exemplary embodiments.

Ninth Exemplary Embodiment

Figure 13:
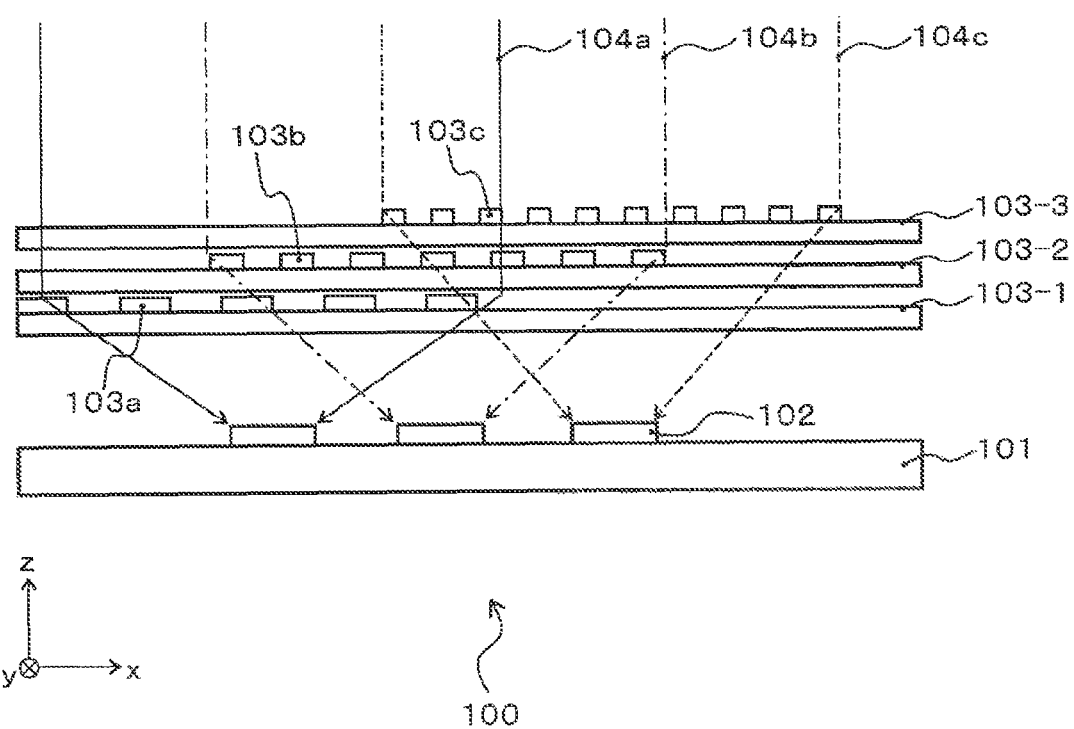

A perspective view of an optical sensor 100 of the present exemplary embodiment is shown by FIG. 1. A plan view of the optical sensor 100 of the present exemplary embodiment is shown by FIG. 3. FIG. 13 is an xz cross-sectional view of the optical sensor 100 of the present exemplary embodiment. The cross-sectional view is that taken on line 2-2' of FIG. 3.

As shown in FIG. 13, at least some of diffraction means in the present exemplary embodiment are each constituted by a convex-concave part. That is, interference fringes are generated by the convex-concave part. In the case of the example shown in FIG. 13, concentric interference fringes are generated by the convex-concave part. By changing the convex-concave pitch according to a wavelength to diffract, a diffraction means for diffracting the desired wavelength can be realized. The height of the convex-concave part is desirably equal to or larger than ¼ of a wavelength to diffract.

In FIG. 13, the diffraction means is constituted by a convex-concave part in every one of the first to third diffraction grating layers 103-1 to 103-3, but the diffraction means may be constituted by a hologram in at least some of the diffraction grating layers. Further, a diffraction means constituted by a convex-concave part and that by a hologram may coexist in the same diffraction grating layer.

In the present exemplary embodiment, the same operation and effect as that of the above-described exemplary embodiments can be realized. While the example shown in FIG. 13 has a configuration based on that of the first exemplary embodiment, an optical sensor 100 of the present exemplary embodiment having the above-described features may also be configured on the basis of the configuration of any one of the third to eighth exemplary embodiments. Also in that way, the above-described operation and effect can be realized.

Hereinafter, supplementary notes will be given on examples of reference embodiments.

1. A sensor unit comprising:
a substrate;
a plurality of light receiving parts arranged on the substrate and for detecting light; and
one or more diffraction grating layers arranged over the substrate and the light receiving parts, the diffraction grating layers having two or more diffraction means each for diffracting light of a corresponding wavelength and thereby condensing the light at a corresponding one of the light receiving parts, wherein:
at least two of the diffraction means are each constituted by a hologram formed in a first one of the diffraction grating layers; and
at least some of the plurality of holograms formed in the first diffraction grating layer each overlap at least partly with other ones of the plurality of holograms neighboring it.

2. The sensor unit according to 1, wherein:
at least one of the diffraction means is formed in a second one of the diffraction grating layers provided on the first diffraction grating layer; and
at least some of the plurality of holograms formed in the first diffraction grating layer each overlap, in the plan view, at least partly with some of the diffraction means formed in the second diffraction grating layer.

3. The sensor unit according to 1 or 2, wherein at least one of the diffraction means is constituted by a hologram or a convex-concave part.

4. The sensor unit according to any one of 1 to 3, wherein the hologram is formed of a material into which intensity distribution of incident light is recorded in the form of refractive index distribution.

5. The sensor unit according to any one of 1 to 4, wherein:
the plurality of light receiving parts include light receiving parts for detecting light of different wavelengths each other, and are divided into a plurality of groups according to the wavelength of light to be detected; and
for a group of light receiving parts having lower sensitivity to light of the target wavelength for their detection, a larger number of diffraction means corresponding to the light receiving parts are provided.

6. The sensor unit according to any one of 1 to 5, wherein:
the plurality of light receiving parts include light receiving parts for detecting light of different wavelengths each other, and are divided into a plurality of groups according to the wavelength of light to be detected; and
the plurality of light receiving parts are arranged such that, for a group of light receiving parts having lower sensitivity to light of the target wavelength for their detection, the total sum of center-to-center spacings, in the lateral direction perpendicular to the thickness direction of the substrate, between diffraction means corresponding to the light receiving parts is larger.

7. The sensor unit according to any one of 1 to 6, further comprising
an optical system for condensing incident light, on the opposite side to the substrate and the light receiving parts across the diffraction grating layers.

8. The sensor unit according to any one of 1 to 7, further comprising
a filter for cutting off light of other wavelengths than a specific wavelength, on the light receiving parts.

9. The sensor unit according to any one of 1 to 8, further comprising
an optical system for condensing incident light, between the diffraction means and the light receiving parts.

10. The sensor unit according to any one of 1 to 9, wherein the light receiving parts are made of a lead zirconate titanate family ceramic material.

This application is based upon and claims the benefit of priority from Japanese Patent Application No. 2013-189462, filed on Sep. 12, 2013, the disclosure of which is incorporated herein in its entirety by reference.

The invention claimed is:
1. A sensor unit comprising:
a substrate;
a plurality of light receiving parts arranged on the substrate and for detecting light; and
one or more diffraction grating layers arranged over the substrate and the light receiving parts, the diffraction grating layers having two or more diffraction units, each of which diffracts light of a corresponding wavelength and thereby condenses the light at a corresponding one of the light receiving parts, wherein:
at least two of the diffraction units are each constituted by a hologram formed in a first one of the diffraction grating layers; and
at least some of the plurality of holograms formed in the first diffraction grating layer each overlap at least partly with some of the plurality of neighboring holograms.

2. The sensor unit according to claim 1, wherein:
at least one of the diffraction units is formed in a second one of the diffraction grating layers provided on the first diffraction grating layer; and
at least some of the plurality of holograms formed in the first diffraction grating layer each overlap, in the plan view, at least partly with some of the diffraction units formed in the second diffraction grating layer.

3. The sensor unit according to claim 2, wherein
at least one of the diffraction units is constituted by a hologram or a convex-concave part.

4. The sensor unit according to claim 2, wherein
the hologram is formed of a material into which intensity distribution of incident light is recorded in the form of refractive index distribution.

5. The sensor unit according to claim 2, wherein:
the plurality of light receiving parts include light receiving parts for detecting light of different wavelengths, and are divided into a plurality of groups according to the wavelength of light to be detected; and
for a group of light receiving parts having lower sensitivity to light of the target wavelength for their detection, a larger number of diffraction units corresponding to the light receiving parts are provided.

6. The sensor unit according to claim 2, wherein:
the plurality of light receiving parts include light receiving parts for detecting light of different wavelengths, and are divided into a plurality of groups according to the wavelength of light to be detected; and
the plurality of light receiving parts are arranged such that, for a group of light receiving parts having lower sensitivity to light of the target wavelength for their detection, the total sum of center-to-center spacings, in the lateral direction perpendicular to the thickness direction of the substrate, between diffraction units corresponding to the light receiving parts is larger.

7. The sensor unit according to claim 1, wherein
at least one of the diffraction units is constituted by a hologram or a convex-concave part.

8. The sensor unit according to claim 7, wherein
the hologram is formed of a material into which intensity distribution of incident light is recorded in the form of refractive index distribution.

9. The sensor unit according to claim 7, wherein:
the plurality of light receiving parts include light receiving parts for detecting light of different wavelengths, and are divided into a plurality of groups according to the wavelength of light to be detected; and
for a group of light receiving parts having lower sensitivity to light of the target wavelength for their detection, a larger number of diffraction units corresponding to the light receiving parts are provided.

10. The sensor unit according to claim 7, wherein:
the plurality of light receiving parts include light receiving parts for detecting light of different wavelengths, and are divided into a plurality of groups according to the wavelength of light to be detected; and
the plurality of light receiving parts are arranged such that, for a group of light receiving parts having lower sensitivity to light of the target wavelength for their detection, the total sum of center-to-center spacings, in the lateral direction perpendicular to the thickness direction of the substrate, between diffraction units corresponding to the light receiving parts is larger.

11. The sensor unit according to claim 1, wherein
the hologram is formed of a material into which intensity distribution of incident light is recorded in the form of refractive index distribution.

12. The sensor unit according to claim 11, wherein:
the plurality of light receiving parts include light receiving parts for detecting light of different wavelengths, and are divided into a plurality of groups according to the wavelength of light to be detected; and
for a group of light receiving parts having lower sensitivity to light of the target wavelength for their detection, a larger number of diffraction units corresponding to the light receiving parts are provided.

13. The sensor unit according to claim 11, wherein:
the plurality of light receiving parts include light receiving parts for detecting light of different wavelengths, and are divided into a plurality of groups according to the wavelength of light to be detected; and
the plurality of light receiving parts are arranged such that, for a group of light receiving parts having lower sensitivity to light of the target wavelength for their detection, the total sum of center-to-center spacings, in the lateral direction perpendicular to the thickness direction of the substrate, between diffraction units corresponding to the light receiving parts is larger.

14. The sensor unit according to claim 1, wherein:
the plurality of light receiving parts include light receiving parts for detecting light of different wavelengths, and are divided into a plurality of groups according to the wavelength of light to be detected; and
for a group of light receiving parts having lower sensitivity to light of the target wavelength for their detection, a larger number of diffraction units corresponding to the light receiving parts are provided.

15. The sensor unit according to claim 1, wherein:
the plurality of light receiving parts include light receiving parts for detecting light of different wavelengths, and are divided into a plurality of groups according to the wavelength of light to be detected; and
the plurality of light receiving parts are arranged such that, for a group of light receiving parts having lower sensitivity to light of the target wavelength for their detection, the total sum of center-to-center spacings, in the lateral direction perpendicular to the thickness direction of the substrate, between diffraction units corresponding to the light receiving parts is larger.

16. The sensor unit according to claim 1, further comprising
an optical system for condensing incident light, on the opposite side to the substrate and the light receiving parts across the diffraction grating layers.

17. The sensor unit according to claim 1, further comprising
a filter for cutting off light of other wavelengths than a specific wavelength, on the light receiving parts.

18. The sensor unit according to claim 1, further comprising
an optical system for condensing incident light, between the diffraction units and the light receiving parts.

19. The sensor unit according to claim 1, wherein
the light receiving parts are made of a lead zirconate titanate family ceramic material.

* * * * *